(12) United States Patent
Meyer (10) Patent No.: US 7,703,599 B2
(45) Date of Patent: Apr. 27, 2010

(54) METHOD AND APPARATUS FOR REVERSING DIRECTION OF AN ARTICLE

(75) Inventor: Thomas C. Meyer, Elkhart Lake, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 397 days.

(21) Appl. No.: 11/104,316

(22) Filed: Apr. 12, 2005

(65) Prior Publication Data

US 2005/0233881 A1    Oct. 20, 2005

Related U.S. Application Data

(60) Provisional application No. 60/563,511, filed on Apr. 19, 2004.

(51) Int. Cl.
*B65G 47/26* (2006.01)
*B31F 1/10* (2006.01)

(52) U.S. Cl. .................. 198/457.03; 198/406; 493/444

(58) Field of Classification Search .............. 198/369.7, 198/369.1, 457.06, 600, 408, 409, 412; 493/444
See application file for complete search history.

(56) References Cited

U.S. PATENT DOCUMENTS

| 135,145 | A | 1/1873 | Murphy |
|---|---|---|---|
| 293,353 | A | 2/1884 | Purvis |
| 312,257 | A | 2/1885 | Cotton et al. |
| 410,123 | A | 8/1889 | Stilwell |
| 432,742 | A | 7/1890 | Stanley |
| 643,821 | A | 2/1900 | Howlett |
| 1,393,524 | A | 10/1921 | Grupe |
| 1,605,842 | A | 11/1926 | Jones |
| 1,686,595 | A | 10/1928 | Belluche |
| 1,957,651 | A | 5/1934 | Joa |
| 2,009,857 | A | 7/1935 | Potdevin |
| 2,054,832 | A | 9/1936 | Potdevin |
| 2,117,432 | A | 5/1938 | Linscott |
| 2,128,746 | A | 8/1938 | Joa |
| 2,131,808 | A | 10/1938 | Joa |
| 2,164,408 | A | 7/1939 | Joa |
| 2,167,179 | A | 7/1939 | Joa |

(Continued)

FOREIGN PATENT DOCUMENTS

BE    1007854    11/1995

(Continued)

*Primary Examiner*—Gene Crawford
*Assistant Examiner*—Ramya Prakasam
(74) *Attorney, Agent, or Firm*—Ryan Kromholz & Manion, S.C.

(57) ABSTRACT

A method of reversing direction of an article is disclosed by engaging an article with a first belt to move the article in a first direction; disengaging the article from the first belt; and then engaging the article with a second belt to move the article in a second direction. An apparatus to reverse direction of an article is also disclosed by a first belt rotating in a first direction; a second belt rotating in a second direction; the first belt engaging an article at a first time while the second belt is disengaged with the article, the first belt disengaging the article at a second time, and the second belt engaging the article at a third time while the first belt is disengaged with the article.

8 Claims, 7 Drawing Sheets

U.S. PATENT DOCUMENTS

| | | |
|---|---|---|
| 2,171,741 A | 9/1939 | Cohn et al. |
| 2,213,431 A | 9/1940 | Joa |
| 2,254,290 A | 9/1941 | Joa |
| 2,254,291 A | 9/1941 | Joa |
| 2,282,477 A | 5/1942 | Joa |
| 2,286,096 A | 6/1942 | Joa |
| 2,296,931 A | 9/1942 | Joa |
| 2,304,571 A | 12/1942 | Joa |
| 2,324,930 A | 7/1943 | Joa |
| 2,345,937 A | 4/1944 | Joa |
| 2,466,240 A | 4/1949 | Joa |
| 2,481,929 A | 9/1949 | Joa |
| 2,510,229 A | 6/1950 | Joa |
| 2,540,844 A | 2/1951 | Strauss |
| 2,584,002 A | 1/1952 | Elser et al. |
| 2,591,359 A | 4/1952 | Joa |
| 2,618,816 A | 11/1952 | Joa |
| 2,702,406 A | 2/1955 | Reed |
| 2,721,554 A | 10/1955 | Joa |
| 2,730,144 A | 1/1956 | Joa |
| 2,772,611 A | 12/1956 | Heywood |
| 2,780,253 A | 2/1957 | Joa |
| 2,785,609 A | 3/1957 | Billeb |
| 2,811,905 A | 11/1957 | Kennedy, Jr |
| 2,839,059 A | 6/1958 | Joa |
| 2,842,169 A | 7/1958 | Joa |
| 2,851,934 A | 9/1958 | Heywood |
| 2,875,724 A | 3/1959 | Joa |
| 2,913,862 A | 11/1959 | Sabee |
| 2,939,461 A | 6/1960 | Joa |
| 2,960,143 A | 11/1960 | Joa |
| 2,990,081 A | 6/1961 | Neui et al. |
| 2,991,739 A | 7/1961 | Joa |
| 3,016,207 A | 1/1962 | Comstock |
| 3,016,582 A | 1/1962 | Joa |
| 3,017,795 A | 1/1962 | Joa |
| 3,020,687 A | 2/1962 | Joa |
| 3,021,135 A | 2/1962 | Joa |
| 3,024,957 A | 3/1962 | Pinto |
| 3,053,427 A | 9/1962 | Wasserman |
| 3,054,516 A | 9/1962 | Joa |
| 3,069,982 A | 12/1962 | Heywood et at |
| 3,086,253 A | 4/1963 | Joa |
| 3,087,689 A | 4/1963 | Heim |
| 3,091,408 A | 5/1963 | Schorneman |
| 3,114,994 A | 12/1963 | Joa |
| 3,122,293 A | 2/1964 | Joa |
| 3,128,206 A | 4/1964 | Dungler |
| 3,203,419 A | 8/1965 | Joa |
| 3,230,955 A | 1/1966 | Joa et al. |
| 3,268,954 A | 8/1966 | Joa |
| 3,288,037 A | 11/1966 | Burnett |
| 3,289,254 A | 12/1966 | Joa |
| 3,291,131 A | 12/1966 | Joa |
| 3,301,114 A | 1/1967 | Joa |
| 3,322,589 A | 5/1967 | Joa |
| 3,342,184 A | 9/1967 | Joa |
| 3,356,092 A | 12/1967 | Joa |
| 3,360,103 A | 12/1967 | Johnson |
| 3,363,847 A | 1/1968 | Joa |
| 3,391,777 A | 7/1968 | Joa |
| 3,454,442 A | 7/1969 | Heller Jr. |
| 3,463,413 A | 8/1969 | Smith |
| 3,470,848 A | 10/1969 | Dreher |
| 3,484,275 A | 12/1969 | Lewicki Jr. |
| 3,502,322 A | 3/1970 | Cran |
| 3,521,639 A | 7/1970 | Joa |
| 3,526,563 A | 9/1970 | Schott, Jr. |
| 3,538,551 A | 11/1970 | Joa |
| 3,540,641 A | 11/1970 | Besnyo et al. |
| 3,575,170 A | 4/1971 | Clark |
| 3,607,578 A | 9/1971 | Berg et al |
| 3,635,462 A | 1/1972 | Joa |
| 3,656,741 A | 4/1972 | Macke et al |
| 3,666,611 A | 5/1972 | Joa |
| 3,673,021 A | 6/1972 | Joa |
| 3,685,818 A | 8/1972 | Burger |
| 3,728,191 A | 4/1973 | Wierzba et al. |
| 3,751,224 A | 8/1973 | Wackerle |
| 3,772,120 A | 11/1973 | Radzins |
| 3,796,360 A | 3/1974 | Alexeff |
| 3,816,210 A | 6/1974 | Aoko et al. |
| 3,847,710 A | 11/1974 | Blomqvist et al |
| 3,854,917 A | 12/1974 | McKinney et al |
| 3,883,389 A | 5/1975 | Schott, Jr. |
| 3,888,400 A | 6/1975 | Wiig |
| 3,903,768 A | 9/1975 | Amberg et al. |
| 3,904,147 A | 9/1975 | Taitel et al. |
| 3,918,698 A | 11/1975 | Coast |
| 3,960,646 A | 6/1976 | Wiedamann |
| 3,991,994 A | 11/1976 | Farish |
| 4,002,005 A * | 1/1977 | Mueller et al. ................ 53/442 |
| 4,003,298 A | 1/1977 | Schott, Jr. |
| 4,009,814 A | 3/1977 | Singh |
| 4,009,815 A | 3/1977 | Ericson et al. |
| 4,053,150 A | 10/1977 | Lane |
| 4,056,919 A | 11/1977 | Hirsch |
| 4,081,301 A | 3/1978 | Buell |
| 4,090,516 A | 5/1978 | Schaar |
| 4,094,319 A | 6/1978 | Joa |
| 4,103,595 A | 8/1978 | Corse |
| 4,106,974 A | 8/1978 | Hirsch |
| 4,108,584 A | 8/1978 | Radzins et al. |
| 4,136,535 A | 1/1979 | Audas |
| 4,141,193 A | 2/1979 | Joa |
| 4,141,509 A | 2/1979 | Radzins |
| 4,142,626 A | 3/1979 | Bradley |
| 4,157,934 A | 6/1979 | Ryan et al. |
| 4,165,666 A | 8/1979 | Johnson et al. |
| 4,168,776 A | 9/1979 | Hoeboer |
| 4,171,239 A | 10/1979 | Hirsch et al. |
| 4,205,679 A | 6/1980 | Repke et al. |
| 4,208,230 A | 6/1980 | Magarian |
| 4,213,356 A | 7/1980 | Armitage |
| 4,215,827 A | 8/1980 | Roberts et al. |
| 4,222,533 A | 9/1980 | Pongracz |
| 4,223,822 A | 9/1980 | Clitheroe |
| 4,231,129 A | 11/1980 | Winch |
| 4,236,955 A | 12/1980 | Prittie |
| 4,275,510 A | 6/1981 | George |
| 4,284,454 A | 8/1981 | Joa |
| 4,307,800 A | 12/1981 | Joa |
| 4,316,756 A | 2/1982 | Wilson |
| 4,325,519 A | 4/1982 | McLean |
| 4,342,206 A | 8/1982 | Rommel |
| 4,364,787 A | 12/1982 | Radzins |
| 4,374,576 A | 2/1983 | Ryan |
| 4,379,008 A | 4/1983 | Gross et al. |
| 4,394,898 A | 7/1983 | Campbell |
| 4,411,721 A | 10/1983 | Wishart |
| 4,452,597 A * | 6/1984 | Achelpohl ................ 493/204 |
| 4,492,608 A | 1/1985 | Hirsch et al. |
| 4,501,098 A | 2/1985 | Gregory |
| 4,508,528 A | 4/1985 | Hirsch et al. |
| 4,522,853 A | 6/1985 | Szonn et al. |
| 4,551,191 A | 11/1985 | Kock et al. |
| 4,586,199 A | 5/1986 | Birring |
| 4,589,945 A | 5/1986 | Polit |
| 4,603,800 A | 8/1986 | Focke et al. |
| 4,614,076 A | 9/1986 | Rathemacher |
| 4,619,357 A | 10/1986 | Radzins et al. |
| 4,634,482 A | 1/1987 | Lammers |
| 4,641,381 A | 2/1987 | Heran et al. |
| 4,642,150 A | 2/1987 | Stemmler |

| Patent | Date | Inventor |
|---|---|---|
| 4,642,839 A | 2/1987 | Urban |
| 4,650,530 A | 3/1987 | Mahoney et al. |
| 4,663,220 A | 5/1987 | Wisneski et al. |
| 4,672,705 A | 6/1987 | Bors et al. |
| 4,675,062 A | 6/1987 | Instance |
| 4,693,056 A | 9/1987 | Raszewski |
| 4,701,239 A | 10/1987 | Craig |
| 4,723,698 A | 2/1988 | Schoonderbeek |
| 4,726,874 A | 2/1988 | VanVliet |
| 4,726,876 A | 2/1988 | Tomsovic et al. |
| 4,743,241 A | 5/1988 | Igaue et al. |
| 4,751,997 A | 6/1988 | Hirsch |
| 4,753,429 A * | 6/1988 | Irvine et al. ............... 270/58.06 |
| 4,756,141 A | 7/1988 | Hirsch et al. |
| 4,764,325 A | 8/1988 | Angstadt |
| 4,765,780 A | 8/1988 | Angstadt |
| 4,776,920 A | 10/1988 | Ryan |
| 4,777,513 A | 10/1988 | Nelson |
| 4,782,647 A | 11/1988 | Williams et al. |
| 4,785,986 A | 11/1988 | Daane et al. |
| 4,795,510 A | 1/1989 | Wittrock et al. |
| 4,798,353 A | 1/1989 | Peugh |
| 4,801,345 A | 1/1989 | Dussaud et al. |
| 4,802,570 A | 2/1989 | Hirsch et al. |
| 4,840,609 A * | 6/1989 | Jones et al. .................... 493/28 |
| 4,845,964 A | 7/1989 | Bors et al. |
| 4,864,802 A | 9/1989 | D'Angelo |
| 4,880,102 A | 11/1989 | Indrebo |
| 4,888,231 A | 12/1989 | Angstadt |
| 4,892,536 A | 1/1990 | DesMarais et al. |
| 4,904,440 A | 2/1990 | Angstadt |
| 4,908,175 A | 3/1990 | Angstadt |
| 4,909,019 A | 3/1990 | Delacretaz et al. |
| 4,925,520 A | 5/1990 | Beaudoin et al. |
| 4,927,322 A | 5/1990 | Schweizer et al. |
| 4,927,582 A | 5/1990 | Bryson |
| 4,937,887 A | 7/1990 | Schreiner |
| 4,963,072 A | 10/1990 | Miley et al. |
| 4,987,940 A | 1/1991 | Straub et al. |
| 4,994,010 A | 2/1991 | Doderer-Winkler |
| 5,000,806 A | 3/1991 | Merkatoris et al. |
| 5,021,111 A | 6/1991 | Swenson |
| 5,025,910 A | 6/1991 | Lasure et al. |
| 5,045,039 A * | 9/1991 | Bay ................................ 493/1 |
| 5,062,597 A * | 11/1991 | Martin et al. ............. 270/39.02 |
| 5,064,179 A * | 11/1991 | Martin ..................... 270/39.02 |
| 5,080,741 A | 1/1992 | Nomura et al. |
| 5,094,658 A | 3/1992 | Smithe et al. |
| 5,096,532 A | 3/1992 | Neuwirth et al. |
| 5,108,017 A | 4/1992 | Adamski et al. |
| 5,109,767 A | 5/1992 | Nyfeler et al. |
| 5,110,403 A | 5/1992 | Ehlert |
| 5,127,981 A | 7/1992 | Straub et al. |
| 5,131,525 A | 7/1992 | Musschoot |
| 5,131,901 A * | 7/1992 | Moll ........................... 493/355 |
| 5,147,487 A | 9/1992 | Nomura et al. |
| 5,163,594 A | 11/1992 | Meyer |
| 5,171,239 A | 12/1992 | Igaue et al. |
| 5,176,244 A | 1/1993 | Radzins et al. |
| 5,183,252 A | 2/1993 | Wolber et al. |
| 5,188,627 A | 2/1993 | Igaue et al. |
| 5,195,684 A | 3/1993 | Radzins |
| 5,203,043 A | 4/1993 | Riedel |
| 5,213,645 A | 5/1993 | Nomura et al. |
| 5,223,069 A | 6/1993 | Tokuno et al. |
| 5,226,992 A | 7/1993 | Morman |
| 5,246,433 A | 9/1993 | Hasse et al. |
| 5,267,933 A * | 12/1993 | Precoma ........................ 493/23 |
| 5,308,345 A | 5/1994 | Herrin |
| 5,328,438 A | 7/1994 | Crowley |
| 5,340,424 A | 8/1994 | Matsushita |
| 5,368,893 A | 11/1994 | Sommer et al. |
| 5,407,513 A | 4/1995 | Hayden et al. |
| 5,415,649 A | 5/1995 | Watanabe et al. |
| 5,421,924 A | 6/1995 | Ziegelhoffer et al. |
| 5,424,025 A | 6/1995 | Hanschen et al. |
| 5,429,576 A | 7/1995 | Doderer-Winkler |
| 5,435,802 A | 7/1995 | Kober |
| 5,449,353 A | 9/1995 | Watanabe et al. |
| 5,464,401 A | 11/1995 | Hasse et al. |
| 5,486,253 A | 1/1996 | Otruba |
| 5,494,622 A | 2/1996 | Heath et al. |
| 5,531,850 A | 7/1996 | Herrmann |
| 5,540,647 A * | 7/1996 | Weiermann et al. ......... 493/444 |
| 5,545,275 A | 8/1996 | Herrin et al. |
| 5,545,285 A | 8/1996 | Johnson |
| 5,552,013 A | 9/1996 | Ehlert et al. |
| 5,556,360 A | 9/1996 | Kober et al. |
| 5,556,504 A | 9/1996 | Rajala et al. |
| 5,560,793 A | 10/1996 | Ruscher et al. |
| 5,586,964 A * | 12/1996 | Chase ........................ 493/413 |
| 5,602,747 A | 2/1997 | Rajala |
| 5,624,420 A | 4/1997 | Bridges et al. |
| 5,624,428 A | 4/1997 | Sauer |
| 5,628,738 A | 5/1997 | Suekane |
| 5,634,917 A | 6/1997 | Fujioka et al. |
| 5,643,165 A | 7/1997 | Klekamp |
| 5,643,396 A | 7/1997 | Rajala et al. |
| 5,645,543 A | 7/1997 | Nomura et al. |
| 5,659,229 A | 8/1997 | Rajala |
| 5,660,657 A | 8/1997 | Rajala et al. |
| 5,660,665 A | 8/1997 | Jalonen |
| 5,683,376 A | 11/1997 | Kato et al. |
| RE35,687 E | 12/1997 | Igaue et al. |
| 5,693,165 A | 12/1997 | Schmitz |
| 5,699,653 A | 12/1997 | Hartman et al. |
| 5,707,470 A | 1/1998 | Rajala et al. |
| 5,711,832 A | 1/1998 | Glaug et al. |
| 5,725,518 A | 3/1998 | Coates |
| 5,745,922 A | 5/1998 | Rajala et al. |
| 5,746,869 A | 5/1998 | Hayden et al. |
| 5,749,989 A | 5/1998 | Linman et al. |
| 5,788,797 A | 8/1998 | Herrin et al. |
| 5,817,199 A | 10/1998 | Brennecke et al. |
| 5,829,164 A | 11/1998 | Kotitschke |
| 5,836,931 A | 11/1998 | Toyoda et al. |
| 5,858,012 A | 1/1999 | Yamaki et al. |
| 5,865,393 A | 2/1999 | Kreft et al. |
| 5,868,727 A | 2/1999 | Barr et al. |
| 5,876,027 A * | 3/1999 | Fukui et al. .................... 270/51 |
| 5,876,792 A | 3/1999 | Caldwell |
| 5,879,500 A | 3/1999 | Herrin et al. |
| 5,902,431 A | 5/1999 | Wilkinson et al. |
| 5,932,039 A | 8/1999 | Popp et al. |
| 5,938,193 A | 8/1999 | Bluemle et al. |
| 5,964,390 A | 10/1999 | Boerresen et al. |
| 5,964,970 A | 10/1999 | Woolwine et al. |
| 6,036,805 A | 3/2000 | McNichols |
| 6,043,836 A | 3/2000 | Kerr et al. |
| 6,050,517 A | 4/2000 | Dobrescu et al. |
| 6,074,110 A | 6/2000 | Verlinden et al. |
| 6,076,442 A | 6/2000 | Arterburn et al. |
| 6,098,249 A | 8/2000 | Toney et al. |
| 6,123,792 A | 9/2000 | Samida et al. |
| 6,183,576 B1 | 2/2001 | Couillard et al. |
| 6,210,386 B1 | 4/2001 | Inoue |
| 6,212,859 B1 | 4/2001 | Bielik, Jr. et al. |
| 6,250,048 B1 | 6/2001 | Linkiewicz |
| 6,264,784 B1 | 7/2001 | Menard et al. |
| 6,276,421 B1 | 8/2001 | Valenti et al. |
| 6,276,587 B1 | 8/2001 | Boerresen |
| 6,306,122 B1 | 10/2001 | Narawa et al. |
| 6,309,336 B1 * | 10/2001 | Muessig et al. ............. 493/444 |
| 6,312,420 B1 | 11/2001 | Sasaki et al. |
| 6,314,333 B1 | 11/2001 | Rajala et al. |
| 6,315,022 B1 | 11/2001 | Herrin et al. |

| | | | | | |
|---|---|---|---|---|---|
| 6,336,921 B1 | 1/2002 | Kato et al. | 2006/0265867 A1 | 11/2006 | Schaap |
| 6,358,350 B1 | 3/2002 | Glaug et al. | 2007/0074953 A1 | 4/2007 | McCabe |

FOREIGN PATENT DOCUMENTS

| | | |
|---|---|---|
| 6,369,291 B1 | 4/2002 | Uchimoto et al. |
| 6,375,769 B1 | 4/2002 | Quereshi et al. |
| 6,391,013 B1 | 5/2002 | Suzuki et al. |
| 6,416,697 B1 | 7/2002 | Venturino et al. |
| 6,443,389 B1 | 9/2002 | Palone |
| 6,446,795 B1 | 9/2002 | Allen et al. |
| 6,473,669 B2 | 10/2002 | Rajala et al. |
| 6,475,325 B1 | 11/2002 | Parrish et al. |
| 6,478,786 B1 | 11/2002 | Glaug et al. |
| 6,482,278 B1 | 11/2002 | McCabe et al. |
| 6,494,244 B2 | 12/2002 | Parrish et al. |
| 6,521,320 B2 | 2/2003 | McCabe et al. |
| 6,524,423 B1 | 2/2003 | Hilt et al. |
| 6,551,228 B1 * | 4/2003 | Richards .................. 493/417 |
| 6,551,430 B1 | 4/2003 | Glaug et al. |
| 6,554,815 B1 | 4/2003 | Umebayashi |
| 6,572,520 B2 | 6/2003 | Blumle |
| 6,581,517 B1 | 6/2003 | Becker et al. |
| 6,596,108 B2 | 7/2003 | McCabe |
| 6,605,172 B1 | 8/2003 | Anderson et al. |
| 6,605,173 B2 | 8/2003 | Glaug et al. |
| 6,637,583 B1 | 10/2003 | Andersson |
| 6,648,122 B1 | 11/2003 | Hirsch et al. |
| 6,649,010 B2 | 11/2003 | Parrish et al. |
| 6,659,150 B1 | 12/2003 | Perkins et al. |
| 6,659,991 B2 | 12/2003 | Suekane |
| 6,675,552 B2 | 1/2004 | Kunz et al. |
| 6,684,925 B2 | 2/2004 | Nagate et al. |
| 6,766,817 B2 | 7/2004 | da Silva |
| D497,991 S | 11/2004 | Otsubo et al. |
| 6,820,671 B2 | 11/2004 | Calvert |
| 6,837,840 B2 * | 1/2005 | Yonekawa et al. .......... 493/444 |
| 6,840,616 B2 | 1/2005 | Summers |
| 6,852,186 B1 | 2/2005 | Matsuda et al. |
| 6,875,202 B2 | 4/2005 | Kumasaka et al. |
| 6,893,528 B2 | 5/2005 | Middelstadt et al. |
| 6,918,404 B2 | 7/2005 | Dias da Silva |
| 6,978,486 B2 | 12/2005 | Zhou et al. |
| 7,066,586 B2 | 6/2006 | da Silva |
| 7,077,393 B2 * | 7/2006 | Ishida .................... 270/37 |
| 7,172,666 B2 | 2/2007 | Groves et al. |
| 7,214,174 B2 | 5/2007 | Allen et al. |
| 7,247,219 B2 | 7/2007 | O'Dowd |
| 2001/0012813 A1 | 8/2001 | Bluemle |
| 2001/0017181 A1 | 8/2001 | Otruba et al. |
| 2002/0046802 A1 | 4/2002 | Tachibana et al. |
| 2002/0059013 A1 | 5/2002 | Rajala et al. |
| 2002/0096241 A1 | 7/2002 | Instance |
| 2003/0000620 A1 | 1/2003 | Herrin et al. |
| 2003/0015209 A1 | 1/2003 | Gingras et al. |
| 2003/0052148 A1 | 3/2003 | Rajala et al. |
| 2003/0066585 A1 | 4/2003 | McCabe |
| 2003/0083638 A1 | 5/2003 | Molee |
| 2003/0084984 A1 | 5/2003 | Glaug et al. |
| 2003/0089447 A1 | 5/2003 | Molee et al. |
| 2003/0135189 A1 | 7/2003 | Umebayashi |
| 2004/0007328 A1 | 1/2004 | Popp et al. |
| 2004/0016500 A1 | 1/2004 | Tachibana et al. |
| 2004/0112517 A1 | 6/2004 | Groves et al. |
| 2004/0164482 A1 | 8/2004 | Edinger |
| 2005/0000628 A1 | 1/2005 | Norrley |
| 2005/0196538 A1 | 9/2005 | Sommer et al. |
| 2005/0230056 A1 | 10/2005 | Meyer et al. |
| 2005/0230449 A1 | 10/2005 | Meyer et al. |
| 2005/0233881 A1 | 10/2005 | Meyer |
| 2005/0234412 A1 | 10/2005 | Andrews et al. |
| 2005/0257881 A1 | 11/2005 | Coose et al. |
| 2005/0275148 A1 | 12/2005 | Beaudoin et al. |
| 2006/0021300 A1 | 2/2006 | Tada et al. |
| 2006/0137298 A1 | 6/2006 | Oshita et al. |
| 2006/0224137 A1 | 10/2006 | McCabe et al. |

| | | |
|---|---|---|
| CA | 1146129 | 5/1983 |
| CA | 1153345 | 9/1983 |
| CA | 1190078 | 7/1985 |
| CA | 1210744 | 9/1986 |
| CA | 1212132 | 9/1986 |
| CA | 1236056 | 5/1988 |
| CA | 1249102 | 1/1989 |
| CA | 1292201 | 11/1991 |
| CA | 1307244 | 9/1992 |
| CA | 1308015 | 9/1992 |
| CA | 1310342 | 11/1992 |
| CA | 2023816 | 3/1994 |
| CA | 2404154 | 10/2001 |
| CA | 2541194 | 4/2006 |
| CA | 2559517 | 5/2007 |
| DE | 102006047280 | 4/2007 |
| EP | 0044206 | 1/1982 |
| EP | 0048011 | 3/1982 |
| EP | 0089106 | 9/1983 |
| EP | 0206208 | 12/1986 |
| EP | 0304140 | 8/1987 |
| EP | 439897 | 2/1990 |
| EP | 455231 | 11/1991 |
| EP | 510251 | 10/1992 |
| EP | 0652175 | 5/1995 |
| EP | 0811473 | 12/1997 |
| EP | 0901780 | 3/1999 |
| EP | 0439897 | 8/1999 |
| EP | 990588 | 4/2000 |
| EP | 1132325 | 9/2001 |
| EP | 1272347 | 1/2003 |
| EP | 1571249 | 9/2005 |
| EP | 1619008 | 1/2006 |
| EP | 1707168 | 4/2006 |
| ES | 509706 | 11/1982 |
| ES | 520559 | 12/1983 |
| ES | 296211 | 12/1987 |
| FR | 2255961 | 7/1975 |
| FR | 2891811 | 4/2007 |
| GB | 191101501 | 1/1912 |
| GB | 439897 | 12/1935 |
| GB | 856389 | 12/1960 |
| GB | 941073 | 11/1963 |
| GB | 1096373 | 12/1967 |
| GB | 1126539 | 9/1968 |
| GB | 1346329 | 2/1974 |
| GB | 1412812 | 11/1975 |
| GB | 2045298 | 10/1980 |
| GB | 2115775 | 9/1983 |
| GB | 2288316 | 10/1995 |
| JP | 428364 | 1/1992 |
| JP | 542180 | 2/1993 |
| JP | 576566 | 3/1993 |
| JP | 626160 | 2/1994 |
| JP | 626161 | 2/1994 |
| JP | 6197925 | 7/1994 |
| JP | 10035621 | 2/1998 |
| JP | 10-277091 | 10/1998 |
| SE | 0602047 | 5/2007 |
| WO | WO 9747810 | 12/1997 |
| WO | WO9907319 | 2/1999 |
| WO | WO9913813 | 3/1999 |
| WO | WO9965437 | 12/1999 |
| WO | WO0143682 | 6/2001 |
| WO | WO0172237 | 10/2001 |
| WO | WO2005075163 | 1/2005 |

\* cited by examiner

METHOD AND APPARATUS FOR REVERSING DIRECTION OF AN ARTICLE

RELATED APPLICATION

This application claims the benefit of U.S. Provisional Patent Application Ser. No. 60/563,511, filed 19 Apr. 2004, and entitled "Method and Apparatus for Reversing Direction of an Article."

BACKGROUND OF THE INVENTION

This invention relates to a method and apparatus for rapidly and accurately reversing direction of a flat article. This invention is not limited to its preferred use, reversing direction of a disposable diaper or sheet of paper; but instead the methods and apparatus' of the present invention may be used in wide ranging applications.

During manufacture of disposable diapers of the children's training pant type, or of the adult incontinence type, manufacturers typically process the diapers through a series of steps. For a variety of reasons, during the manufacturing process, it might be necessary to reverse direction of the article, from forward to reverse, or from forward to upside down to reverse, or from forward to downward etc.

SUMMARY OF THE INVENTION

The present invention is used, for example, to controllably reverse the direction of the leading edge of a diaper panel as it is being cross folded. Typical cross folders used on high speed diaper lines may produce extremely high deceleration and reversal forces in the free tail end of the product being folded. One advantage provided by this invention is to reduce the acceleration forces felt by the product as it goes through the reversal process, by first carrying the article in a first direction by way of contact with the surface of a belt system which is moving in the first direction. At a point slightly before the expected reversal, the forward moving belt nip is opened and a reverse moving belt nip is engaged so that the product is stopped and then driven backwards by the second belt.

The present invention is particularly useful for products that may not be able to withstand high deceleration forces. For instance, a fluff filled adult diaper moving at a speed of more than 1000 feet per minute is stopped nearly instantly when it is cross folded. It has been calculated that the end of the product is subjected to accelerations as high as 65 Gs or 637 meters per second. The fluff contents of such a diaper could very well be destroyed by a "crack the whip" effect. The reversing conveyor of the present invention provides a controlled and driven reversal, wherein the product itself is not subjected to the same distribution of forces.

In one embodiment of the present invention, the positions of the conveyors or conveyor belts are swapped, reversed, or alternated using eccentric hubs on conveyor pulleys. Rotating the shaft that drive the eccentric hubs changes the effective centerline of these pulleys. In one embodiment, the eccentricity is such that rotating the shaft 180 degrees opens the outgoing belt nip and closes the ingoing belt nip. In another embodiment, the shafts are arranged so as to shift only one of the two belts, but each belt having its own dedicated shaft system. This would allow for the opening of one nip and the closing of the other nip to be adjustable relative to the other.

A method of reversing direction of an article is disclosed by engaging an article with a first belt to move the article in a first direction; disengaging the article from the first belt; and then engaging the article with a second belt to move the article in a second direction. An apparatus to reverse direction of an article is also disclosed by a first belt rotating in a first direction; a second belt rotating in a second direction; the first belt engaging an article at a first time while the second belt is disengaged with the article, the first belt disengaging the article at a second time, and the second belt engaging the article at a third time while the first belt is disengaged with the article.

These steps and advantages will be more evident with the following detailed description and drawings.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention.

Figure 1:
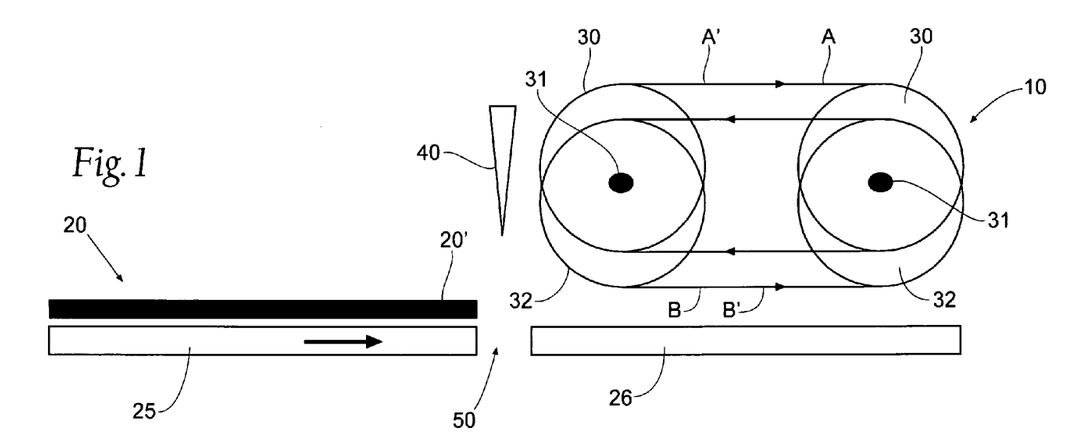
FIG. 1 is a side view of an apparatus for reversing direction of an article, showing a first belt operating in a first direction, a second belt operating in a second direction, and an article whose direction is desired to be reversed.

Referring now FIG. 1, a side view is shown of an apparatus 10 for reversing direction of an article 20, showing a first belt B operating in a first direction B', a second belt A operating in a second direction A'. The article 20, which may be a diaper in a preferred use of one embodiment of the apparatus 10 and method of the present invention, approaches the apparatus 10 for instance by use of a conveyor 25, as depicted the article 20 moving to the right. As is common in the art, a cross folder 40, is used and will be described later to crimp the article 20 to encourage folding.

As will be discussed later, belt A may be carried by conveyor pulleys 30, belt B may be carried by conveyor pulleys 32. However, more or less conveyor pulleys may be utilized, or means other than belts A and B may be used to engage the article 20, such as nips, drums, or any other conveying means known in the art.

Figure 2:
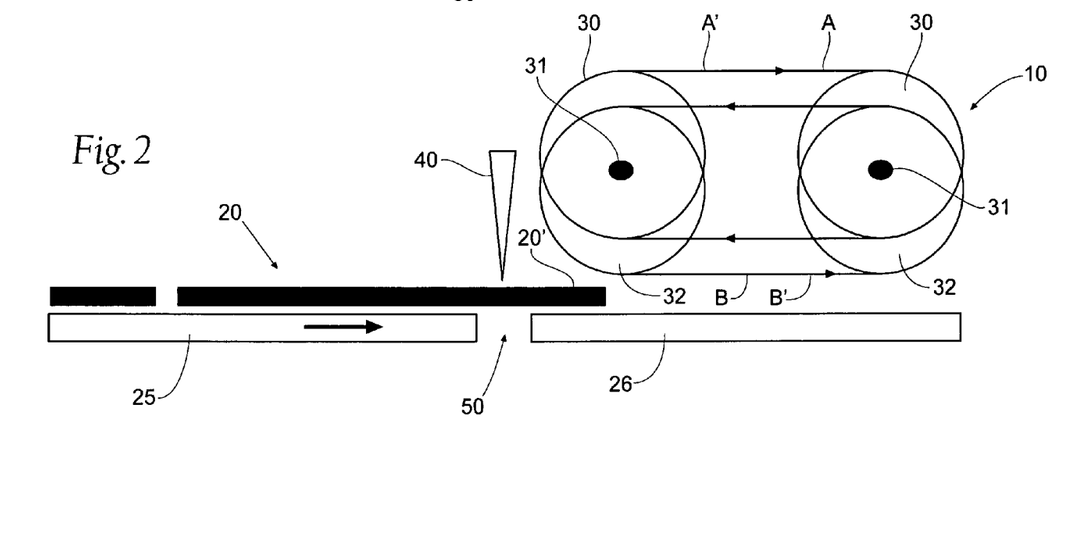
FIG. 2 is a side view of the apparatus, with the article whose direction is desired to be reversed approaching the belts.

Referring now to FIG. 2, typical cross folders used on high speed diaper lines such as shown in FIG. 2 may produce extremely high deceleration and reversal forces in the free tail end 20' of the product being folded 20. To reduce the acceleration forces felt by the product 20 as it goes through the reversal process, depicted in the drawings as first forward to the right, reversing to second direction vertical downward, the article 20 is first carried the first direction (right as shown) by the conveyor 25, and then by engagement with contact with the surface of belt B moving in the first direction B'. (For clarity of illustration, the belts A and B are not shown directly engaged with the article 20, but instead showing slight separation that may or may not be present in physical embodiments of the present invention). Still referring to FIG. 2, the cross folder 40 is shown approaching the article 20 to encourage folding of the article 20, the article 20 being supported by both conveyor 25 and stationary surface 26.

Figure 3:
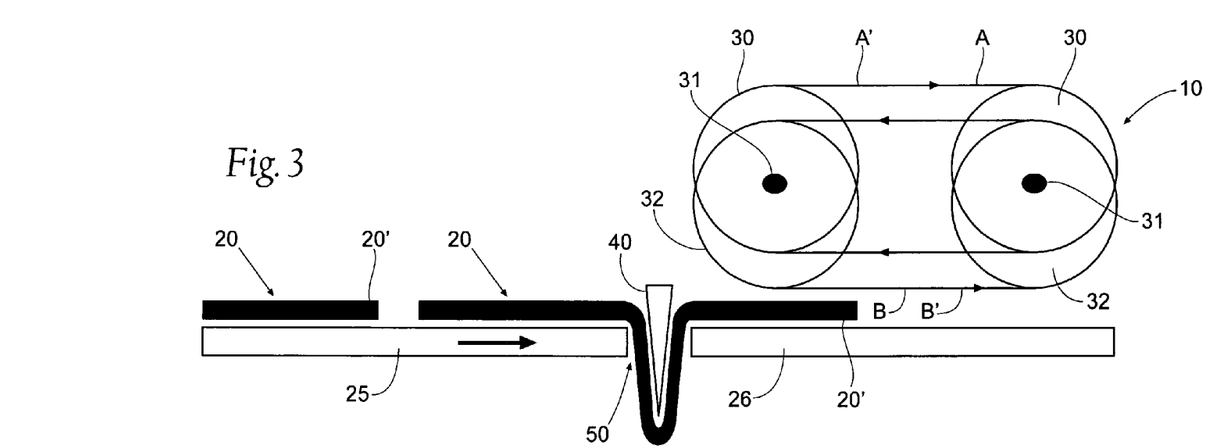
FIG. 3 is a side view of the apparatus, with the article whose direction is desired to be reversed being engaged by the first belt.

Referring now to FIG. 3, the cross folder 40 is shown impacting the article 20, both encouraging folding, and also sending a portion of the article downward through void 50 down its later expected path. At this point, the article 20 is still moving to the right as shown, both by conveyor 25 and by belt B moving in direction B'.

Figure 4:
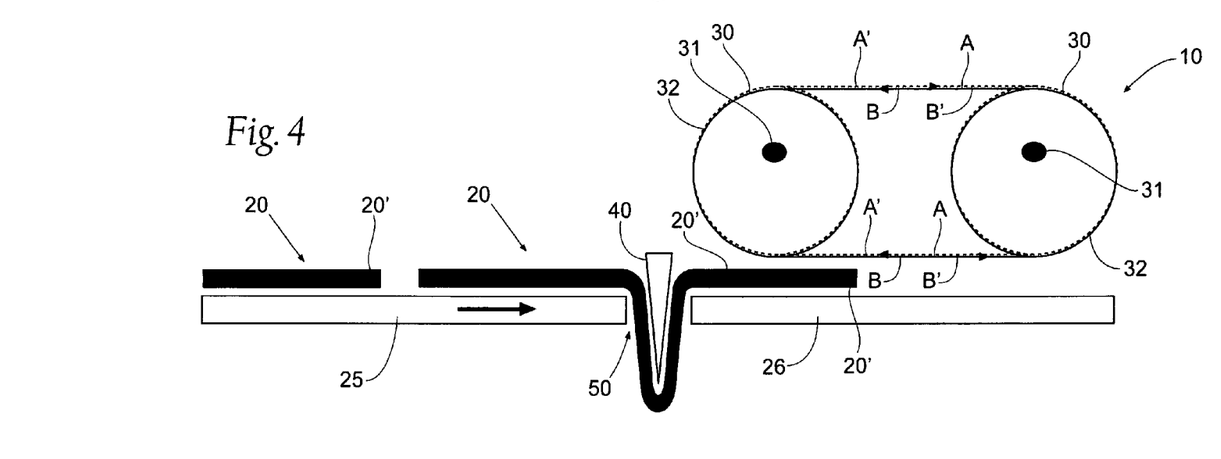
FIG. 4 is a side view of the apparatus, with the article whose direction is desired to be reversed being disengaged by the first belt and the second belt approaching the article for engagement.

Referring now to FIG. 4, at a point slightly before the expected reversal of the tail end 20' of the article 20, the belt B has disengaged with the article 20 and belt A moving in direction A' (reverse direction of B') is approaching the article 20. At this point, cross folder 40 remains positioned as earlier in relation to the article 20.

Without the present invention, products that may not be able to withstand high deceleration forces would be exposed to very high deceleration at this point of reversal. For instance, a fluff filled adult diaper moving at a speed of more than 1000 feet per minute is stopped nearly instantly when it is cross folded. It has been calculated that the free end 20' of the product 20 would have been subjected to accelerations as high as 65 Gs or 637 meters per second. The fluff contents of such a diaper could very well be destroyed by a "crack the whip" effect. The reversing conveyor of the apparatus 10 provides a controlled and driven reversal, wherein the article 20 is not subjected to the same distribution of forces.

Figure 5:
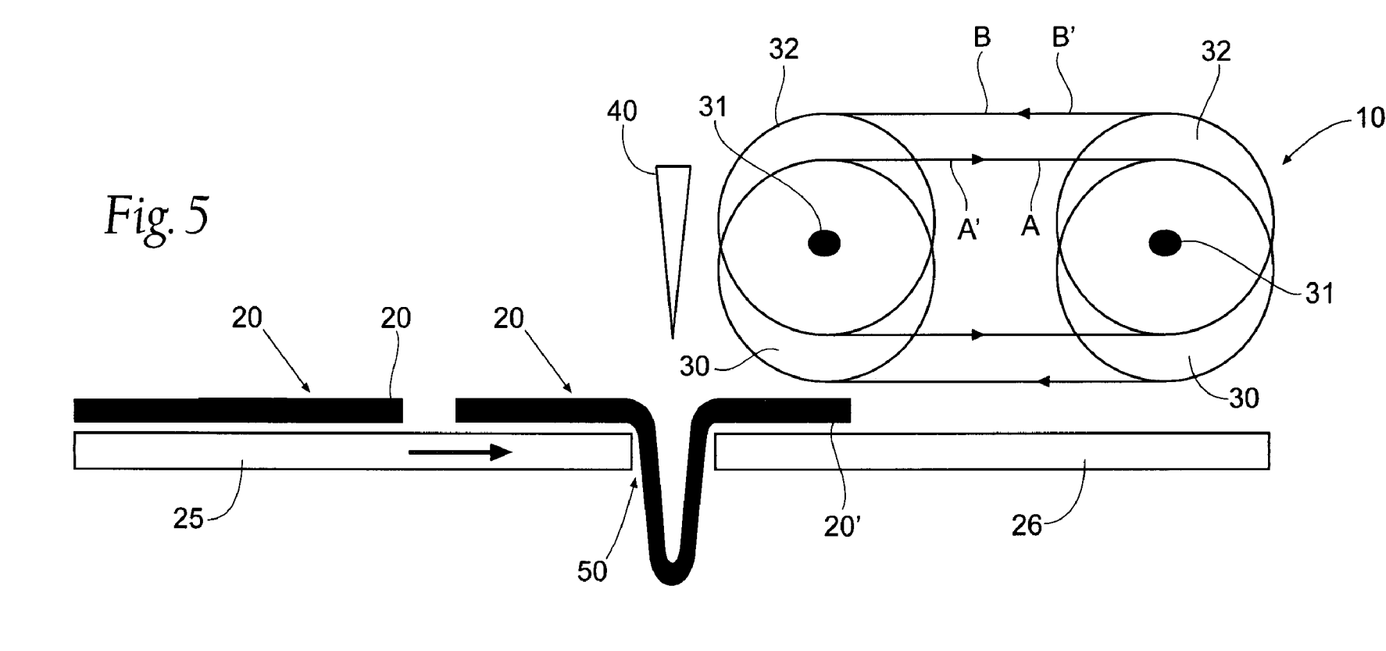
FIG. 5 is a side view of the apparatus, with the article whose direction has been reversed by engagement with the second belt.

Referring now to FIG. 5, belt A has engaged the free end 20' of the article 20, and the free end 20' of the article 20 is stopped and then driven backwards by the second belt A moving in direction A'. At this point, the two ends of the article 20 are moving toward each other, and the direction of the free end 20' of the article 20 has been successfully reversed. At this point, cross folder 40 is being withdrawn from the article 20.

Figure 6:
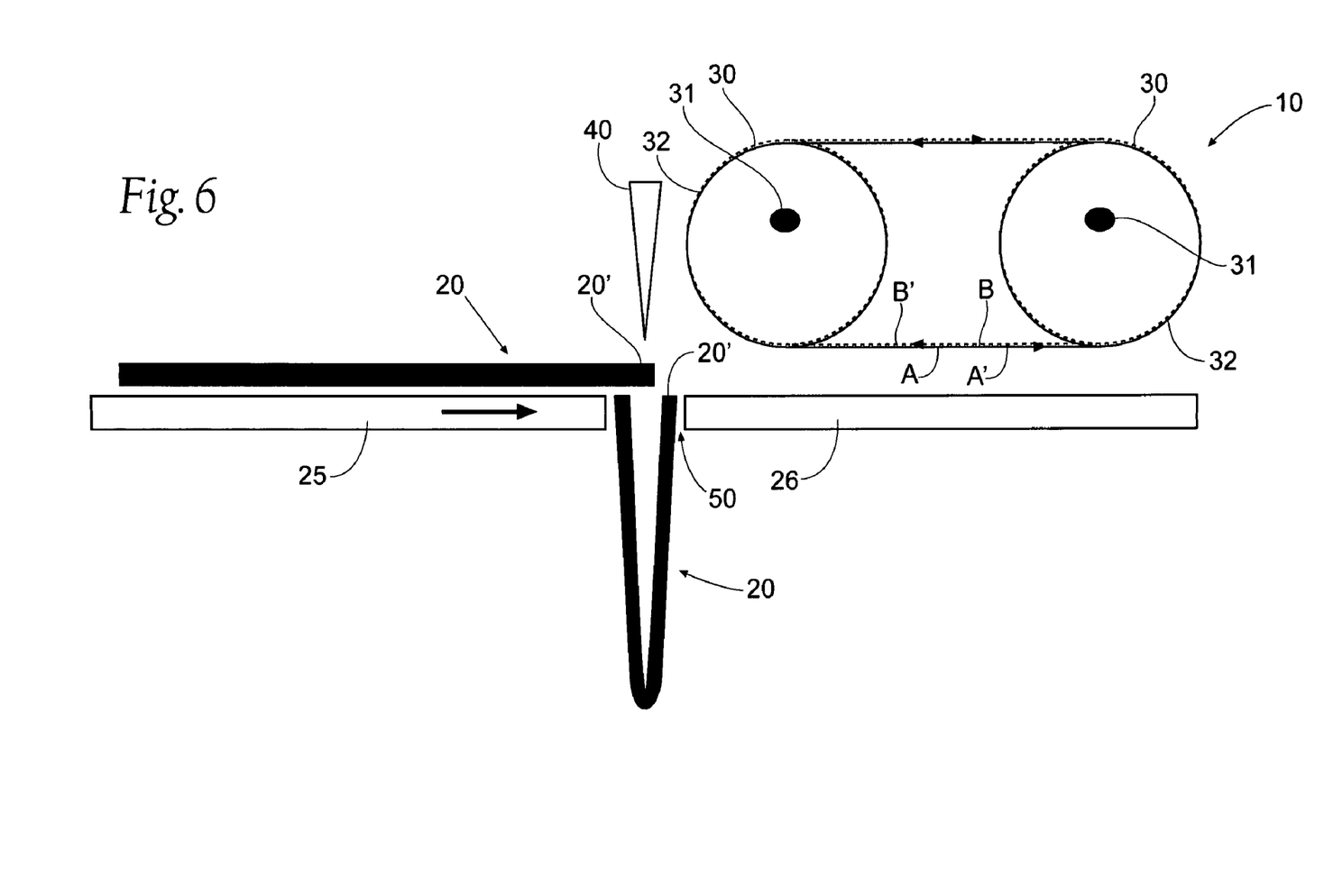
FIG. 6 is a side view of the apparatus, with the article whose direction has been reversed being disengaged by the second belt and discharged, and a second article approaching the apparatus for reversal.

Referring now to FIG. 6, a side view of the apparatus 10 is shown, with the article 20 whose direction has been reversed being disengaged by the second belt A and discharged through the void 50. At this point, a second article 20 is approaching the apparatus 10 for its eventual reversal as described above.

Figure 7:
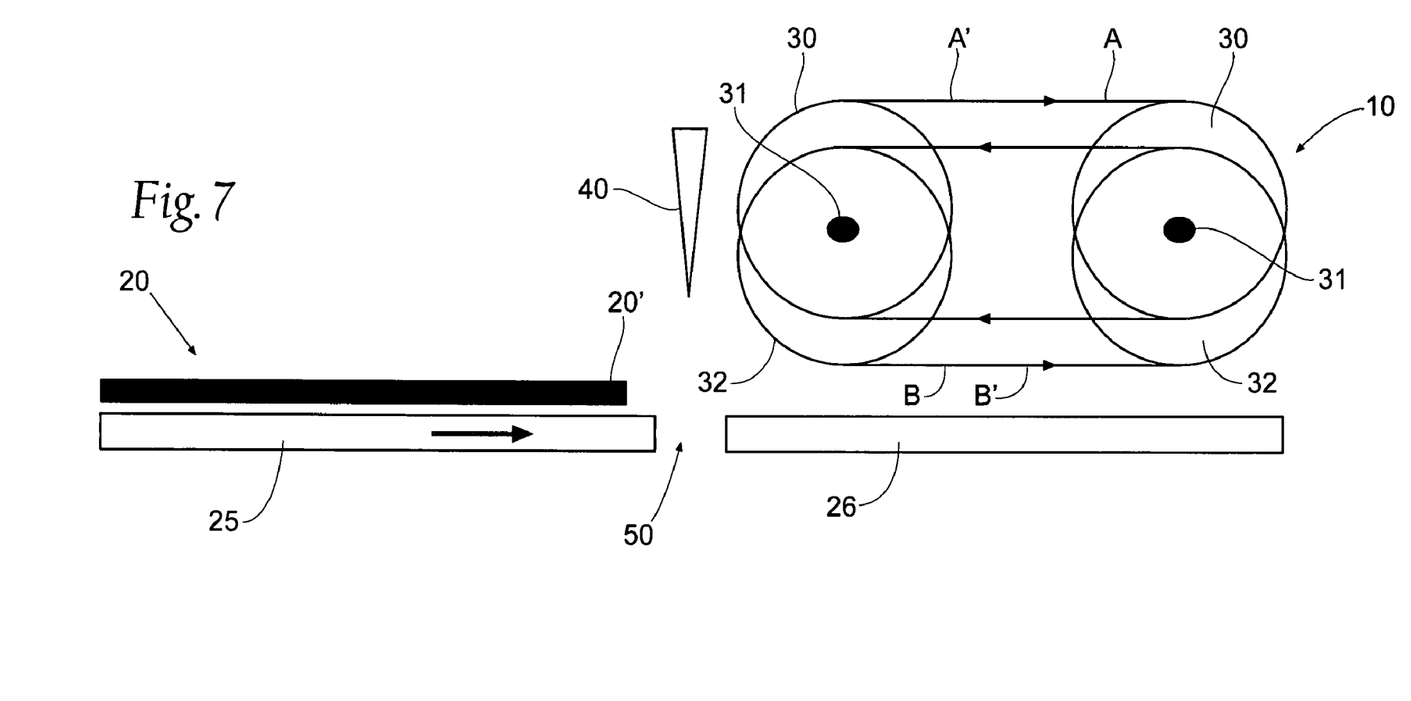
FIG. 7 is a side view of an apparatus for reversing direction of an article, showing a first belt operating in a first direction, a second belt operating in a second direction, and an article whose direction is desired to be reversed.

Referring now to FIG. 7, a side view of the apparatus 10 is shown, and the apparatus has returned to the same condition depicted in FIG. 1, prepared to reverse the direction of the second article 20, the direction of first article 20 already being changed, first article 20 continuing down its intended path for further processing.

There are several timing and synchronization considerations to consider in the operation of the apparatus 10. First, the timing of the cross folder 40 is preferably such that the cross folder cycles once for each article 20 passed through the apparatus 10. It may be preferable to time the cross folder 40 to impact the article 20 in the middle of the article 20, but this may be varied in accordance with user preference.

Another timing consideration is that it is preferred that each belt A and B operate in a speed equal to the conveyor 25. This is preferred because the free end 20' will be traveling the same speed in the same direction B' as its opposing end while engaged by belt B. This is also preferred so that both ends, free end 20' and its opposing end are traveling toward void 50 in opposite directions while free end 20' is being engaged by belt A. Therefore belt A and conveyor 25 should be traveling the same speed in the same direction, while belt B and conveyor 25 should be traveling the same speed in opposite directions.

Another timing consideration is that folded reversed articles 20 should be withdrawn from the apparatus 10 at the same rate as unfolded articles 20 enter the apparatus 10.

As a last timing consideration, each cycle of the present methodology comprises one article 20 being fed into the apparatus 10, engaging the article 20 with belt B, disengaging belt B while engaging the article with belt A, then discharging article 20. Therefore, for each cycle, belts A and B, and cross folder 40 act in synchronization of one engagement per cycle. The operation and implementation of these synchronization considerations is well known in the art and will not be described herein.

In one embodiment of the present invention, conveyors or conveyor belts A and B are reversed using eccentric hubs 30 and 32. Rotating the shaft 31 that drive the eccentric hubs 30 and 32 changes the effective centerline of these pulleys. In one embodiment, the eccentricity is such that rotating the shaft 31 180 degrees engages belt A disengages belt B. In another embodiment (not shown), shafts are arranged so as to shift only one of the two belts A or B, but each belt A and B having its own dedicated shaft system. This would allow for the opening of one nip and the closing of the other nip to be adjustable relative to the other.

Figure 8:
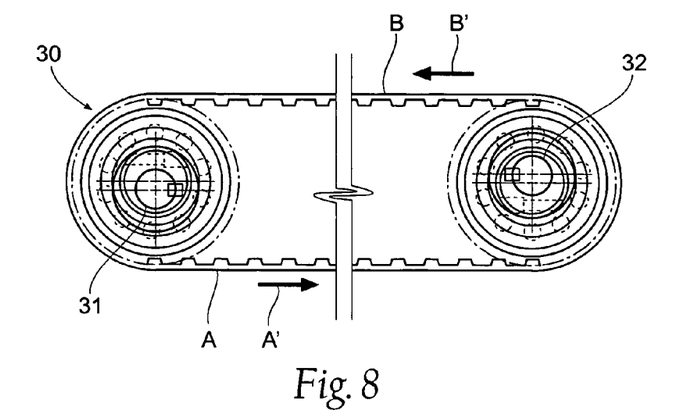
FIG. 8 is a side view of one embodiment of a conveyor and conveyor pulleys, and an eccentric shaft.

Referring now to FIG. 8, conveyor belts A and B are shown driven by hubs 30 and 32.

Figure 9:
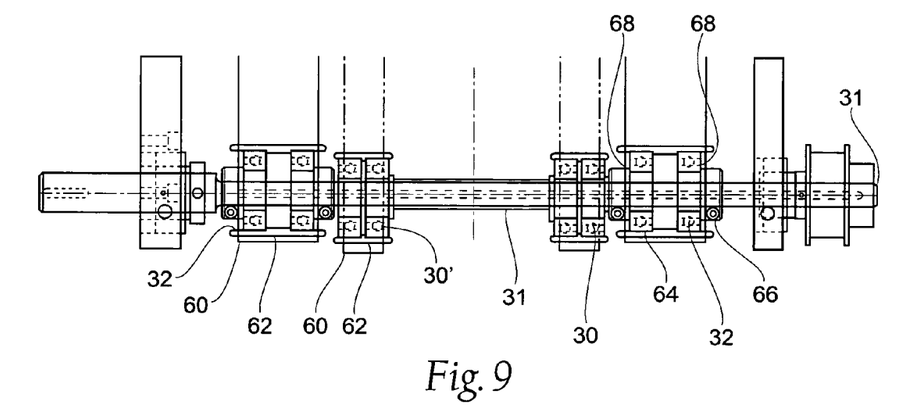
FIG. 9 is a side view of an eccentric shaft coupled with four conveyors and conveyor pulleys.

Referring now to FIG. 9, another side view is shown of the shaft 31 carrying hubs 30 and 32 (4 shown). Also shown are timing belts 60, rollers 62, ball bearings 64, collars clamps 66, and cams 68 it being understood that each hub 30 and 32 may be similarly equipped. In the view shown, it can be seen that hubs 30, situated between hubs 32, are in the lower position. Rotating shaft 31, would cause hubs 30 to raise, while also causing hubs 32 to lower. In this sense, the shaft 31 rotatably causes the first hub 30 and said second hub 30 and 32 to alternately raise and lower.

Figure 10A:
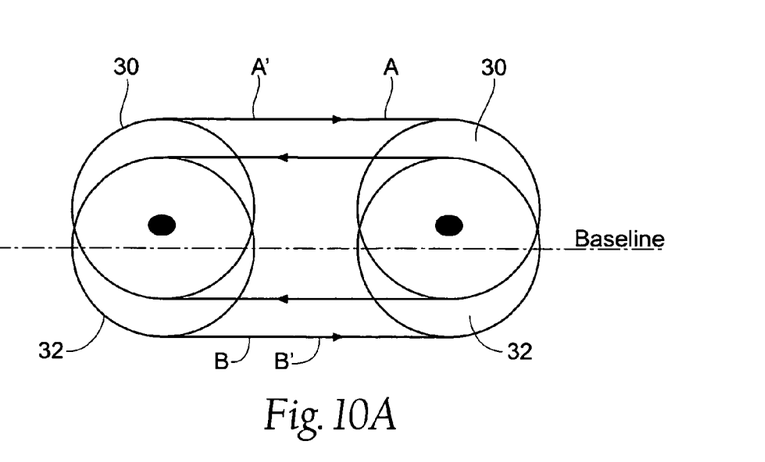
FIGS. 10a and 10b are side views of an alternate embodiment of an apparatus for reversing direction of an article, showing a first belt operating in a first direction, a second belt operating in a second direction, the first belt stationary and the second belt oscillating up and down to engage an article.
Figure 10B:
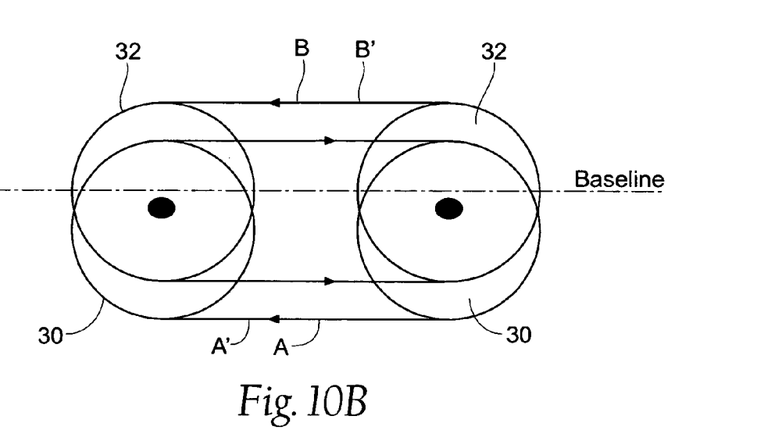

Referring now to FIGS. 10a and 10b side views of an alternate embodiment of an apparatus for reversing direction of an article are shown. In this embodiment, a first belt A operates in a first direction A' as previously described, and a second belt B operating in a second direction B' as previously described. In this embodiment however, the hubs 32 remain stationary vertically relative to the baseline pictured, and the hubs 30 move up and down vertically relative to the baseline to engage an article (not shown). In this manner, the belts A and B still alternately engage the article and the engagement, including the maneuvering of the cross folder 40, the belt 25 and other timing aspects remain the same as in the maneuvering of the hubs 30 and 32 synchronously as described above.

Figure 11:
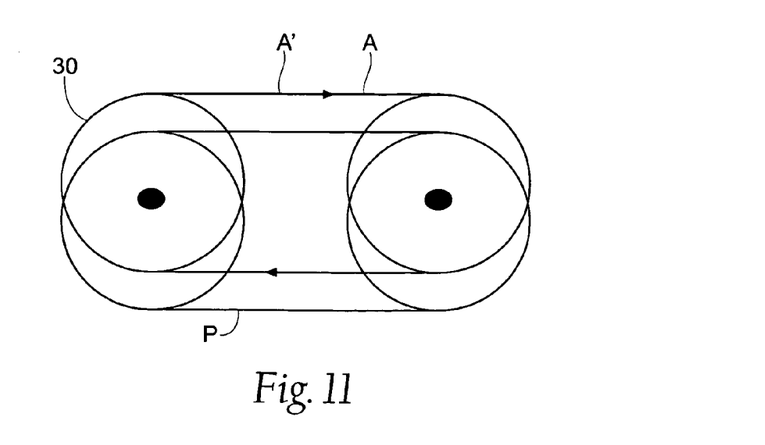
FIG. 11 is a side view of another alternate embodiment showing a first belt operating in a first direction; a plate for engaging an article to discourage movement in a direction different than that encouraged by the belt.

Referring now to FIG. 11, an alternate embodiment of an apparatus for reversing direction of an article is shown, showing a first belt A operating in a first direction A', and a plate P that is not required to rotate with reference to previously described belts. In this embodiment, there is only directional assistance applied to the article 20 in one direction (A'), and the belt A is drawn into contact 20 with product (not shown) when directional reversal is required.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention.

I claim:

1. An apparatus for reversing direction of an article comprising:
   a first belt rotating in a first direction;
   a second belt rotating in a second direction, opposite said first direction;
   said first belt engaging a first side of said article during a first time period of contact to urge said article in a forward direction;
   said second belt engaging said first side of said article during a second time period of contact, said second time period of contact after said first period of contact to urge said article in a reverse direction, opposite of said forward direction;
   said first and said second belts driven by an eccentric hub, to move said article in said forward direction and next in said reverse direction.

2. An apparatus according to claim 1, said apparatus further comprising a conveyor to carry said article toward said first and second belts.

3. An apparatus according to claim 2, said conveyor operating in said forward direction.

4. An apparatus according to claim 2, said conveyor carrying said article during said first period of contact and said second period of contact.

5. An apparatus according to claim 1, the apparatus further comprising a cross folder for engaging said article.

6. An apparatus according to claim 1, the cross folder engaging said article during at least one of said first and said second periods of contact.

7. An apparatus according to claim 1, the apparatus further comprising a surface for carrying said article during said first and second periods of contact.

8. An apparatus for reversing direction of an article comprising:
   a conveyor for carrying an article towards a belt, said article having a leading and a trailing edge;
   a surface for carrying said article, said surface underneath said belt;
   said conveyor operating in a forward direction,
   said belt operating in a reverse direction, said reverse direction opposite said forward direction;
   wherein a void space receives said article;
   wherein a cross folder directs said article into said void space;
   said trading edge traveling in said forward direction while said cross folder is directing said article;
   said leading edge traveling in said reverse direction while said cross folder is directing said article; said leading edge urged in said reverse direction by said belt, between said belt and said surface.

* * * * *